United States Patent [19]
Paz

[11] Patent Number: 5,515,859
[45] Date of Patent: May 14, 1996

[54] MYOCARDIAL INFARCTION AND ISCHEMIA DETECTION METHOD AND APPARATUS

[75] Inventor: Frederick M. Paz, Mokelumne Hill, Calif.

[73] Assignee: Colorado Health Care Research Corp., Lakewood, Colo.

[21] Appl. No.: 111,972

[22] Filed: Aug. 24, 1993

[51] Int. Cl.⁶ ............................. A61B 5/00; A61B 5/097
[52] U.S. Cl. ..................... 128/719; 128/633; 128/664; 128/730; 250/339.01; 250/341.1; 250/341.5; 250/341.8; 250/343; 422/84
[58] Field of Search ................. 128/653.1, 719, 128/730, 633, 664; 250/340, 341, 343, 345, 341.1, 341.5, 341.8, 339.01; 422/84

[56] References Cited

U.S. PATENT DOCUMENTS

| | | | |
|---|---|---|---|
| 3,824,079 | 7/1974 | Venema | 422/84 |
| 3,867,099 | 2/1975 | Forrester | 422/84 |
| 4,083,367 | 4/1978 | Portner et al. | 128/725 |
| 4,169,465 | 10/1979 | Walls et al. | 128/719 |
| 4,233,842 | 11/1980 | Raemer et al. | 128/719 |
| 4,485,822 | 12/1984 | O'Connor et al. | 128/719 |
| 4,850,371 | 7/1989 | Broadhurst et al. | 128/719 |
| 4,907,166 | 3/1990 | Corrrenmann et al. | 128/719 |
| 4,966,141 | 10/1990 | Bacaner et al. | 128/719 |
| 5,022,406 | 6/1991 | Tomlinson | 128/730 |
| 5,055,268 | 10/1991 | Martin | 422/84 |
| 5,092,342 | 3/1992 | Hattendorff et al. | 128/719 |
| 5,095,913 | 3/1992 | Yelderman et al. | 128/719 |
| 5,104,859 | 4/1992 | Sollevi | 514/46 |
| 5,111,827 | 5/1992 | Rantala | 128/719 |
| 5,117,830 | 6/1992 | McAfee et al. | 128/654 |
| 5,129,401 | 7/1992 | Corenmann et al. | 128/716 |
| 5,130,544 | 7/1992 | Nilsson | 250/343 |
| 5,143,695 | 9/1992 | Van den Burg | 422/84 |
| 5,146,092 | 9/1992 | Apperson et al. | 250/343 |
| 5,213,109 | 5/1993 | Susi | 128/719 |
| 5,261,415 | 11/1993 | Dussault | 422/84 |
| 5,296,706 | 3/1994 | Braig et al. | 250/339 |
| 5,299,579 | 4/1994 | Gedeon et al. | 128/719 |
| 5,309,921 | 5/1994 | Kisner et al. | 128/719 |

OTHER PUBLICATIONS

Jones, "Possible Interference by Common Odiferous Foodstuffs in the determination of Breath–Alcohol Content Using the Intoxilyzer 4011 AS", Dec. 2, 1988, pp. 34–36, 38–40, 43–45 and Fig. 2–3.

Nakanishi et al., "Infrared Absorption Spectroscopy", 2d, cover page and pp. 1–7, 73–77, 1977.

*Primary Examiner*—Krista M. Zele
*Attorney, Agent, or Firm*—Bernhard Kreten

[57] ABSTRACT

A device (10) for detecting a substance in a patient's expired breath (88) such as adenosine indicative of cardiovascular distress. The device (10) shines an infrared light (68) through a chamber (14) containing the breath (88) to a detector (26). The detector (26) measures the intensity of the light (68) at selected frequency corresponding to absorption bands of the substance. Multiple photodetectors (112, 114, 116, 118) at different absorption band frequencies increase the specificity of detection. A reference chamber (16) containing a reference gas and coupled to an infrared photodetector (118) may be used to provide a baseline reference for a quantitative analysis.

23 Claims, 2 Drawing Sheets

MYOCARDIAL INFARCTION AND ISCHEMIA DETECTION METHOD AND APPARATUS

FIELD OF THE INVENTION

The present invention relates to the detecting of a substance in an expired air sample. More specifically, the present invention pertains to the detection of myocardial infarction, ischemia, or both by detecting a substance in the expired air sample of a patient which is indicative of cardiovascular distress.

BACKGROUND OF THE INVENTION

When a physician is assessing a patient who may be experiencing acute myocardial infarction or ischemia, the physician needs accurate data quickly to properly diagnose the patient, and most importantly, to provide the appropriate treatment.

The current "state of the art" methods for detecting or confirming acute myocardial infarction or ischemia involve the considering of a combination of factors. This diagnosing can include analyzing cardiac enzymes such as creatinine phosphokinase (CPK), analyzing the patient's electrocardiogram (ECG), in addition to analyzing patient signs and symptoms.

Unfortunately, these methods have an inherent time delay to acquire the data, thus delaying any treatment decision which relies on the data. For example, sequential enzyme assays and ECGs both consume precious time. As will be discussed in more detail below, the delay of even a few minutes can greatly decrease the effectiveness and benefits associated with therapies such as thrombolytic drugs.

Furthermore, extensive training and experience is required to accurately interpret ECGs. Even with such extensive training and experience, ECG findings can be nonspecific.

Although cardiac catheterization is accurate and reliable, in most cases it is not available in a timely fashion in that it requires both proper medical facilities and a cardiologist and is thus typically impractical.

Studies have shown that both the short term benefit and the long term benefit achieved by thrombolytic therapy are closely related to the therapy's early initiation. However, although thrombolytic therapy has a relatively large benefit-to-risk ratio, its associated risks of hemorrhage, especially intracerebral hemorrhage, mandates that a high probability exists for acute myocardial ischemia or infarction to be present before thrombolytic therapy is used.

Currently, the average time between a patient's arrival in an emergency room and the initiation of thrombolytic therapy is slightly greater than one hour. The necessary acquisition or interpretation of multiple laboratory tests by a physician after the patient arrives in the emergency department accounts for the greatest percentage of this time. Reducing the time to initiate thrombolytic therapy will require diagnostic testing which is rapid, relatively sensitive and specific for acute myocardial infarction and ischemia. Such testing will require a minimum of patient cooperation and will yield results which require a limited amount of skill and experience.

What is needed, then, is a practical, accurate, quick and relatively inexpensive method of diagnosing acute myocardial infarction and ischemia, which can reduce the time between the initial contact with a patient and the time the patient receives appropriate therapy.

The prior art listed on the appended list of prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

Yelderman, U.S. Pat. No. 5,095,913 is directed to a capnograph for measuring the absolute concentrations of constituents in a patient's respiratory air stream.

Walls et al., U.S. Pat. No. 4,169,465 is directed to a method and apparatus for obtaining cardio-pulmonary measurements using a rebreathing technique. A patient breathes a gas containing selected trace gases in a closed system. The concentrations of these trace gases is detected and recorded over time.

Neither Yelderman nor Walls et al. discloses that cardiovascular distress produces a telltale substance which may be detected in a patient's expired air stream. Furthermore, neither reference discloses apparatus for detecting such a substance.

SUMMARY OF THE INVENTION

This invention is based on the premise that certain telltale substances are released by a patient in response to certain types of cardiac distress. Some of these substances are contained in the patient's expired air.

Adenosine is a chemical metabolite produced endogenously by myocardial tissue. Most recently, it has been produced synthetically for therapeutic purposes and is well identified by many analytical methods. It is a potent physiological vasodilator of the coronary vascular system and is released in large quantities during episodes of acute blood flow compromise to the cardiac tissue.

Adenosine's half-life in the body is extremely short, estimated to be less than ten seconds, being degraded to inosine, hypoxanthine and adenosine monophosphate. This rapid rate of elimination from the system makes it an excellent marker for acute events which prompt its production.

The pulmonary vasculature and alveolar system is at a point midway between the point of greatest concentration of adenosine, that is, myocardial venous drainage system, and the target tissue, that is, the myocardial arterial system. The greater the demand on myocardial oxygen consumption ($MVO_2$), the greater the concentration of adenosine in the pulmonary vasculature and also in the pulmonary alveolar gaseous mixture.

A device according to the present invention enables an operator of limited experience and training to obtain an expired air sample in the appropriate clinical setting, for analysis, perform the analysis and interpret the results in a rapid fashion.

The device is non-invasive, the unit is compact and mobile, and the results are essentially immediate. The design allows for simultaneous and continuous measurements of the metabolic constituents released during myocardial ischemia or infarction which diffuse into the alveolar gaseous mixture and are present in the expired gaseous mixture.

A device according to the present invention detects a substance in a patient's expired breath indicative of cardiovascular distress. The device includes a sample chamber which receives and contains the patient's expired breath. A light source is positioned to shine a light into the sample chamber. A light detector is positioned to detect the light after it has traversed the sample chamber and provides a signal corresponding to the intensity of the light detected at a predetermined frequency, where the predetermined frequency corresponds to an absorption band of the substance. In response, an indication is provided to the operator of the presence of the substance in the breath sample.

In a preferred embodiment of the present invention, infrared light is used for the detection. Furthermore, the device may optionally include multiple light detectors which provide signals corresponding to the intensity of light detected at different absorption bands of the substance to increase the specificity of detection.

The light detectors may include optical bandpass filters centered on the different absorption bands and a photodetector which receives the light after it has passed through a filter.

Optionally, the device may include a reference chamber which also has an associated light detector which receives the light after it has traversed the reference chamber. The light detector provides a reference signal which corresponds to the intensity of light detected at the same frequency as a light detector for the sample chamber. In such case, the indicator provides an indication of the difference between the signal from the sample chamber and the signal from the reference chamber.

A method for detecting substance in a patient's expired breath indicative of compromise blood flow to the patient's heart according to the present invention includes shining a light through a sample of breath. The intensity of light at a predetermined frequency is measured, where the frequency corresponds to an absorption band of the substance to be detected.

The method may be used with infrared light and at multiple frequencies corresponding to different absorption bands of the substance.

The method and apparatus of the present invention also can determine rapidly when myocardial oxygen demand has been satisfied, by treatment intervention, in the setting of acute myocardial ischemia or infarction by appreciating a sequential decrease in the level of the said substance.

By using the qualitative and quantitative aspects of infrared spectroscopy and the unique absorption and transmission characteristics of adenosine to infrared radiation, a gaseous mixture from a patient with suspected myocardial ischemia or infarction can be rapidly and accurately analyzed to confirm the diagnosis and proceed with appropriate therapy, which would enhance both the short and long term outcomes in these patients.

OBJECTS OF THE INVENTION

It is a principal object of the present invention to provide a method and apparatus for detecting the presence of a select substance in a gaseous mixture by analysis of an air sample.

A further object is to provide rapid diagnosis of the existence of acute myocardial infarction and ischemia.

If is a further object of the present invention to provide a method and apparatus for detecting the presence and/or concentration of a select substance of unique infrared absorption pattern in a gaseous mixture by using infrared spectroscopic analysis of an expired air sample which emanates from a patient. It is yet another object of the present invention to provide immediate objective "bedside" information which accurately reflects metabolic demand of the myocardium and myocardial oxygen consumption ($MVO_2$) as is present in the clinical setting of myocardial infarction and ischemia.

Viewed from a first vantage point it is an object of the present invention to provide a device for detecting in a patient's expired breath a substance indicative of cardiovascular distress, comprising: a sample chamber adapted to receive and contain the breath; means to analyze the breath communicating with the sample chamber for the existence of the substance; and display means operatively couple to the analyzing means to provide an output correlative to the existence of the substance.

Viewed from a second vantage point, it is an object of the present invention to provide a method for diagnosing cardiovascular distress, the steps including: sampling expired breath; analyzing the breath for a telltale correlative of the distress; and displaying results of the analyzing step.

These and other features, advantages, and objects of the present invention will be made more clear when considering the following specification when taken in conjunction with the appended drawings.

DESCRIPTION OF PREFERRED EMBODIMENTS

Figure 1:
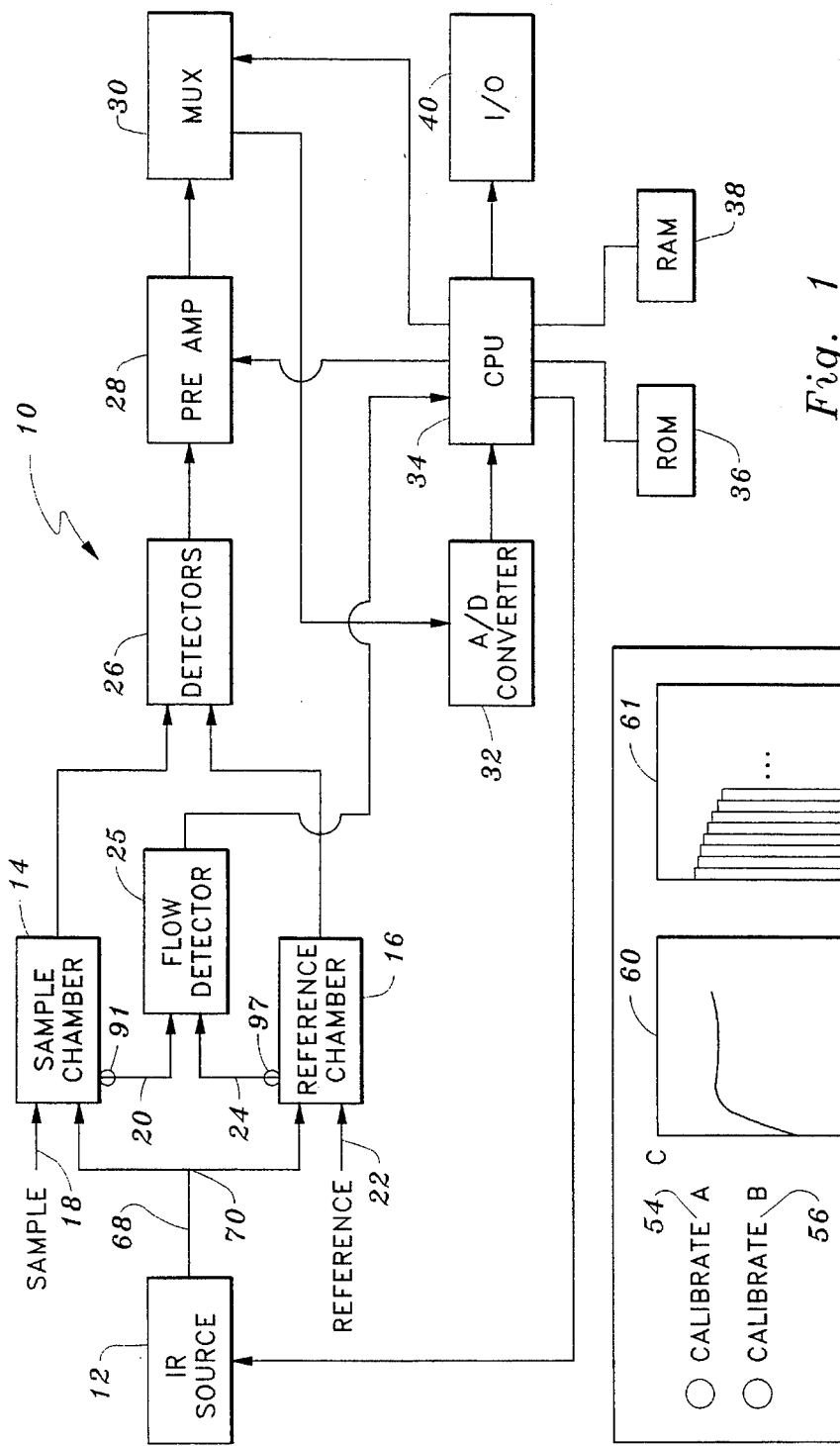
FIG. 1 shows a block diagram of a myocardial infarction and ischemia detecting device according to the present invention.

Referring now to the drawings; wherein like reference numerals denote like elements throughout the various drawings, reference numeral 10 is directed to an acute myocardial infarction and ischemia detecting device according to the present invention.

The device 10 comprises an infrared source 12 which shines infrared light through a sample chamber 14 and a reference chamber 16. The sample chamber has a sample inlet 18 and a sample outlet 20. Likewise, the reference chamber has a reference inlet 22 and a reference outlet 24. Located at the sample outlet 20 and the reference outlet 24 is a flow detector 25 which provides a signal when flow is detected.

The light from the infrared source 12 passes through the sample chamber 14 and the reference chamber 16 to a plurality of detectors 26. The physical arrangement of the infrared source 12, the sample chamber 14, the reference chamber 16 and the detectors 26 will be discussed in more detail below in connection with FIG. 1.

The detectors 26 provide signals to pre-amplifiers 28. The amplitude of the signals correspond to the intensities of infrared light they detect in different respective frequency bandwidths. The preamplifiers amplify and level shift the signals they receive and provide the resulting signals to a multiplexer 30. The multiplexer 30 provides a selected one of its inputs to a analog-to-digital (A/D) converter 32. The A/D converter 32 converts the signal at its input to digital form and provides it to a central processing unit (CPU) 34.

The CPU 34 commands the infrared source 12 to emit light and also receives the signal from the flow detector 25. The CPU controls which input signal to the multiplexer 30 is provided to the A/D converter 32. The CPU also controls the amounts of gain and level shifting done by the preamplifiers 28. The CPU has its program instructions stored in read-only memory (ROM) 36 and has associated random access memory 38. Displays and input switches 40 allow an operator to control the device 10.

Figure 2:
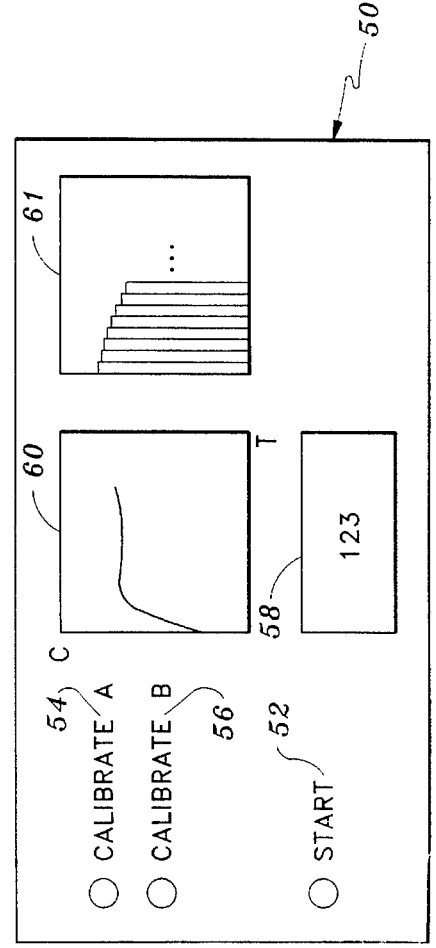
FIG. 2 shows an exemplary control panel for the device of FIG. 1.

Referring now to FIG. 2, an exemplary control panel for the acute myocardial infarction and ischemia detecting device 10 is shown. The control panel includes various input switches. A START switch 52 enables the operator to initiate operation of the device. CALIBRATE A and CALIBRATE B switches, 54, 56 respectively are used in calibrating the device, which will be discussed below. A numeric display 58 shows the concentration of adenosine detected in a patient's breath sample 18. A graphical display 60 shows the detected concentration for a single breath as a function of time. A rise in the concentration indicates that the gas present in the sample chamber 14 is being displaced by the patient's breath and that the breath contains a concentration of adenosine. Analysis of the sample chamber contents will be continuous as the sample breath displaces gas from the sample chamber. As end tidal volume is reached, the concentration of adenosine will plateau on the graphic display confirming acquisition of a sample breath representative of an alveolar gaseous mixture.

A second graphical display 61 shows the level of plateaus for multiple breaths. This allows the physician to detect a change in maximum adenosine concentration over various intervals.

Figure 3:
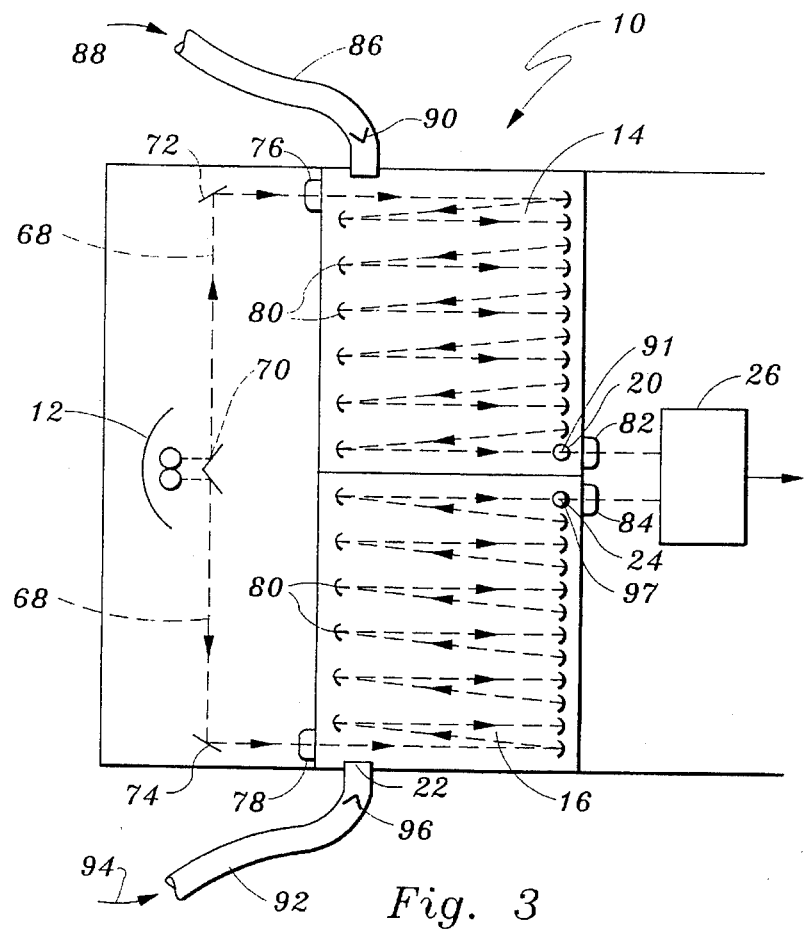
FIG. 3 shows an interior view of the sample and reference chambers of the device of FIG. 1.

Referring now to FIG. 3, light 68 from the infrared source 12 is directed by a beam splitter 70 and two mirrors 72, 74 to the sample chamber 14 and the reference chamber 16. The light enters the sample chamber 14 and the reference chamber 16 through optical windows 76 and 78, respectively. Once inside the chambers, the light is reflected by a plurality of mirrors 80, lengthening the light path through the volume of each chamber. The mirrors are arranged such that the light paths through the sample and reference chambers are equally long. The light exits the sample chamber 14 and the reference chamber 16 through optical windows 82 and 84, respectively, and strikes the detectors 26. The detectors 26 will be discussed in more detail below in connection with FIG. 4.

The four optical windows 76, 78, 82, and 84 optionally may incorporate lenses to focus and collect the infrared light 68 before detection.

A length of tubing 86 (FIG. 3) defines the FIG. 1 sample inlet 18 and carries the sample gaseous mixture 88 to the sample chamber 14. A one-way, low-resistance valve 90 prevents back-flow contamination. When the mixture enters the sample chamber, the displaced gas exits through the sample outlet 20. Another one-way, low resistance valve 91 located at the sample outlet maintains the sample gaseous mixture in the sample chamber. A flow detector 25 (shown in FIG. 1) coupled to the sample outlet 20 provides a signal to the CPU 34 when flow is detected.

Likewise, a length of tubing 92 (FIG. 3) defines the FIG. 1 reference inlet 22 and carries the reference gaseous mixture 94 to the reference chamber 16. A one-way, low-resistance valve 96 prevents back-flow contamination. When the mixture enters the reference chamber, the displaced gas exits through the reference outlet 24. Another one-way, low resistance valve 97 located at the reference outlet maintains the reference gaseous mixture in the reference chamber. A flow detector 25 (shown in FIG. 1) coupled to the reference outlet 24 provides a signal to the CPU 34 when flow is detected.

Preferably, the lengths of tubing 86, 92 are permeable to water vapor, allowing the humidity of the gaseous mixtures to decrease and thereby minimize condensation in the sample and reference chambers 14, 16. The volumes of the tubing 86 and chamber 14 preferably are sufficiently small so that a patient's expired breath completely displaces the volume of air in the chamber 14. Exemplary volumes are 150 milliliters (ml) for the tubing and 250 ml for a single chamber.

Figure 4:
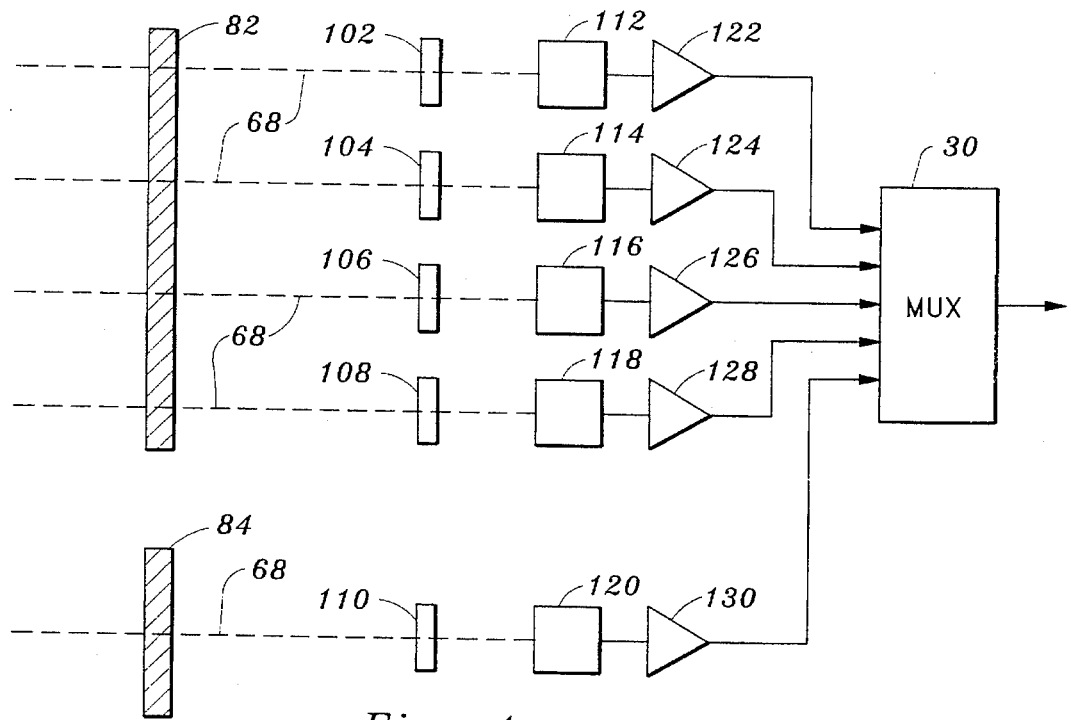
FIG. 4 shows a schematic diagram of the detectors of the device of FIG. 1.

Referring now to FIG. 4, infrared light 68 from the sample and reference chambers 14, 16 passes through the optical windows 82, 84. The light then passes through optical bandpass filters 102, 104, 106, 108, and 110. The optical bandpass filters 102, 104, 106, and 108 associated with the sample chamber have center frequencies selected to coincide with absorption bands of adenosine in the infrared range. Four such frequencies correspond to 1300 $cm^{-1}$, 1580 $cm^{-1}$, 1610 $cm^{-1}$, and 2880 $cm^{-1}$ wavenumbers. (The $cm^{-1}$ wavenumber dimension refers to the number of wavelengths in one-tenth centimeter.) The one-half power corner bandwidth of the bandpass filters is 20 $cm^{-1}$ wavenumbers from the center wavenumber.

The center frequency of the bandpass filter 110 associated with the reference chamber 16 preferably corresponds to a 1580 $cm^{-1}$ wavenumber. The one-half power corner bandwidth of the reference bandpass filter also is 20 $cm^{-1}$ wavenumbers from the center wavenumber.

After passing through the optical bandpass filters 102, 104, 106, 108, 110, the infrared light 68 impinges on respective photodetectors 112, 114, 116, 118, and 120. The photodetectors provide signals corresponding to the intensity of light received by the detectors to respective preamplifiers 122, 124, 126, 128, and 130 (referred to generally in FIG. 1 by reference number 26). As discussed above, the preamplifiers amplify and level-shift the signals from the photodetectors and provide the resulting signals to the multiplexer 30.

For convenience, the detector elements associated with a single frequency of detection are termed herein as a "channel" of the detector. For example, optical bandpass filter 104, photodetector 114, and preamplifier 124 make up one channel of the detector.

The absorbance "A" is related to the initial intensity of light "$I_0$" and the final intensity of light "$I_F$" according to the Beer Equation.

$$A = \log_{10}(I_O/I_F) \quad (1)$$

The transmittance "T" is related to the initial and final intensities of light according to the Lambert Equation.

$$T = I_F/I_O \quad (2)$$

Furthermore, since the absorbance "A" is related to the percent transmittance "%T" according to $$A = \log_{10}(\%T) \quad (3)$$

and $$A = abC \quad (4)$$

where "a" is an absorption constant, "b" is the absorption path length, and "C" is the concentration of the sample, then the concentration can be expressed as $$C = \frac{-\log_{10}(I_O/I_F)}{ab} \quad (5)$$

Since the absorption constant "a," the absorption path length "b," and the initial light intensity $I_0$ are all knowable, and the final light intensity $I_F$ is what is being measured, the concentration "C" can be calculated.

To use the acute myocardial infarction and ischemia detecting device, a patient is instructed to blow into the tubing 86 attached to the sample chamber 14. The expired air enters the sample chamber 14, displacing the air already present. The displaced air exits through the one-way valve 91 located at the sample outlet 20. The flow detector 25 signals the central processing unit 34 to begin controlling the preamplifiers 28 and the multiplexer 30. When the CPU has the measured intensity data from one of the channels, equation (5) given above can be used to calculate the concentration of adenosine in the patient's breath.

Preferably, data from each channel of the detector 26 is used to determine whether adenosine is present in the sample, or merely another substance that happens to share an absorption band with adenosine. In an exemplary embodiment, if the calculations for one of the channels determines a concentration of adenosine more than five percent different from calculations for the other channels, then the operator would be signaled that an error had occurred. Due to the potentially harmful side-effects of thrombolytic treatment, it is preferable to error on the side of false negative determinations instead of false positive determinations.

The reference chamber 16 may be used to establish a baseline to be subtracted from the adenosine concentration calculated solely from the sample chamber. The operator may blow into the tubing 92 attached to the reference input 22. The expired air enters the reference chamber 16, displacing the air already present. The displaced air exits through the one-way valve 97 located at the reference outlet 24. The flow detector 25 signals the central processing unit 34 to begin controlling the preamplifiers 28 and the multiplexer 30. When the central processing unit 34 measures the intensity data from the sample channels, it also measures the intensity detected by the reference photodetector 120. Since the operator presumably has no adenosine in his breath, any value of adenosine calculated from his breath is an erroneous offset and should be subtracted from those concentration calculated for the sample chamber 14. Alternatively, ambient air may be used to fill the reference chamber.

Alternatively, a single chamber may by used to serve the function of both the sample chamber 14 and the reference chamber 16. All five channels depicted in FIG. 4 would be placed in a single chamber, the sample chamber; the need for a separate reference chamber would be eliminated. One channel of the detectors and corresponding bandpass filter could be centered outside an absorption band of adenosine to serve as the reference and baseline channel. For example, optical bandpass filter 110 (FIG. 4) could be centered at 1550 cm$^{-1}$ wavenumbers. Any absorption or reflectance of the infrared light 68 occurring at this frequency would be caused by other environmental factors such as pollen, dust, water vapor, and such, but not by adenosine. Thus, the decrease in light intensity detected by photodetector 120 could be factored into the calculations of adenosine concentration for the other channels.

The device may be calibrated by filling the sample chamber with a gaseous mixture having a known concentration of adenosine. By using two different mixtures having different concentrations, the device can determine an appropriate measurement gain constant $k_1$ and offset $k_2$ to be incorporated into Equation (5).

$$C = \frac{-k_1 \cdot \log_{10}(I_O/I_F) - k_2}{ab} \quad (6)$$

For example, the sample chamber 14 would first be filled with a mixture having no adenosine. The operator would then activate the CALIBRATE A switch 54 (FIG. 2), commanding the device to calibrate itself for such a mixture. To do so, the device would attempt to measure the adenosine concentration in the mixture using Equation (6) with $k_1$ equal to 1 and $k_2$ equal to 0. A nonzero resulting value would be the amount of error introduced by the measuring system and is stored as offset $k_2$ to be subtracted from subsequent calculations. Next, the operator would fill the sample chamber 14 with a mixture having a predetermined concentration of synthesized adenosine and then would activate the CALIBRATE B switch 56. In response, the device would again attempt to measure the adenosine concentration in the mixture using Equation (5). The offset $k_2$ determined in the first calibration step would be subtracted. The gain constant $k_1$ would then be adjusted such that the calculation results in the known concentration of adenosine. The gain and offset constants $k_1$ and $k_2$ may be stored in nonvolatile memory to be used in subsequent measurements. The calibration steps may be repeated at any time to recalibrate the device.

The present invention has been described in reference to a specific hardware layout having specific characteristics. It will be obvious to one of appropriate skill in the art that many modifications may be made to the device which would result in similar results. For example, multiple infrared sources may be used for the different chambers rather than a single source. Also, a single chamber may be used to serve the functions of both the sample chamber 14 and the reference chamber 16. A different type of detector 26 may be used which relies upon another sensing technique such as refraction for determining the absorption spectrum of the gaseous mixture. Furthermore, a different arrangement of circuitry may be used to process the output from the detectors. Such an arrangement could be hardwired analog and digital circuitry rather than the disclosed general purpose multiplexer 30, A/D converter 32, and CPU 34.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A device for detecting adenosine in a patient's expired breath indicative of cardiovascular distress, comprising:

a sample chamber adapted to receive and contain the patient's expired breath;

a light source positioned to shine a light into the sample chamber;

a first light detector positioned to detect the light at a first predetermined frequency after it has traversed the sample chamber, the first light detector providing a first signal corresponding to the intensity of the light detected at said first predetermined frequency, where the first predetermined frequency corresponds to a first absorption band of adenosine; and indicator means, responsive to the first signal, for providing an indication of the value of the first signal.

2. The device of claim 1, wherein said light source shines infrared light.

3. The device of claim 2, further comprising a second light detector positioned to detect the light at a second predetermined frequency after it has traversed the sample chamber, the second light detector providing a second signal corresponding to the intensity of the light detected at said second predetermined frequency, where the second predetermined frequency corresponds to a second absorption band of adenosine.

4. The device of claim 3, wherein at least one of said light detectors comprises an optical bandpass filter and a photodetector arranged such that the light travels through said optical bandpass filter before striking said photodetector.

5. The device of claim 4, wherein said optical bandpass filter has a center frequency of 1300 cm$^{-1}$ wavenumbers which corresponds to an absorption band of adenosine.

6. The device of claim 4, wherein said optical bandpass filter has a center frequency of 1580 cm$^{-1}$ wavenumbers which corresponds to an absorption band of adenosine.

7. The device of claim 4, wherein said optical bandpass filter has a center frequency of 1610 cm$^{-1}$ wavenumbers which corresponds to an absorption band of adenosine.

8. The device of claim 4, wherein said optical bandpass filter has a center frequency of 2880 cm$^{-1}$ wavenumbers which corresponds to an absorption band of adenosine.

9. The device of claim 1, further comprising a reference chamber to receive and contain a reference gas, wherein said light source is positioned to shine said light into said reference chamber, and further comprising a reference light detector positioned to detect said light at said first predetermined frequency after it has traversed said reference chamber, said reference light detector providing a reference signal corresponding to an intensity of said light detected at the first predetermined frequency and wherein said indicator means comprises means responsive to the reference signal for providing an indication of the difference between the value of the first signal and the value of the reference signal.

10. A method for detecting adenosine in a patient's expired breath indicative of cardiovascular distress, the method comprising:
    containing the breath;
    shining a light through the breath;
    detecting the light after it has passed though the breath;
    providing a first signal corresponding to an intensity of the light detected at a first predetermined frequency, where the first predetermined frequency corresponds to a first absorption band of adenosine; and
    indicating the value of the signal.

11. The method of claim 10, wherein the shining step includes shining light in the infrared range.

12. The method of claim 10, further comprising providing a signal corresponding to the intensity of the light detected at a second predetermined frequency, where the second predetermined frequency corresponds to a second absorption band of adenosine.

13. The method of claim 10 further including providing a reference signal and comparing the reference signal to the first signal.

14. A device for detecting adenosine in a patient's expired breath indicative of cardiovascular distress, comprising:
    a sample chamber to receive and contain the breath;
    means for analyzing the breath contained within said sample chamber for the existence of the adenosine; and
    display mean operatively coupled to said analyzing means to provide an output correlative to the existence of the adenosine.

15. The device of claim 14 further comprising means to initialize said device including reference means for receiving an exemplar having initializing qualities, said reference means coupled to said analyzing means and
    comparing means coupled to said analyzing means to receive data therefrom whereby said device will have been initialized.

16. The device of claim 15 wherein said analyzing means includes plural sensors, each said sensor tuned to a different characteristic of adenosine to render less likely a false positive reading.

17. The device of claim 16 further including means to sense the initiation of said detector including a flow meter coupled both to said sample chamber and a central processor control unit, whereby said device is enabled when breath expired by the patient triggers said flow meter to actuate said central processor control unit.

18. A method for diagnosing cardiovascular distress, the steps including:
    sampling expired breath;
    analyzing the breath for adenosine; and
    displaying results of the analyzing step.

19. A method for diagnosing cardiovascular distress, the steps including:
    sampling expired breath;
    analyzing the breath for a telltale correlative of the distress; and
    displaying results of the analyzing step,
    including initializing the diagnostic procedure by comparing the breath with a known reference.

20. The method of claim 19 including sensing the expired breath with multiple sensors, thereby providing multiple characteristics of the expired breath to minimize false positives.

21. A device for detecting a substance in a patient's expired breath indicative of cardiovascular distress, comprising:
    a sample chamber to receive and contain the breath;
    means for analyzing the breath contained within said sample chamber for the existence of the substance;
    display means operatively coupled to said analyzing means to provide an output correlative to the existence of the substance;
    means to initialize said device including reference means for receiving an exemplar having initializing qualities;
    said reference means coupled to said analyzing means;
    comparing means coupled to said analyzing means to receive data therefrom whereby said device will have been initialized;
    said analyzing means including plural sensors, each said sensor tuned to a different characteristic of the substance to render less likely a false positive reading; and
    means to sense the initiation of said detector including a flow meter coupled both to said sample chamber and a central processor control unit whereby said device is enabled when breath expired by the patient triggers said flow meter to actuate said central processor control unit.

22. A device for detecting a substance in a patient's expired breath indicative of cardiovascular distress, comprising:
    a sample chamber to receive and contain the breath;
    means for analyzing the breath contained within said sample chamber for the existence of the substance;
    display means operatively coupled to said analyzing means to provide an output correlative to the existence of the substance;

means to initialize said detector; and means to sense the initiation of said detector including a flow meter coupled both to said sample chamber and a central processor control unit, whereby said device is enabled when breath expired by the patient triggers said flow meter to actuate said central processor control unit.

23. A method for determining the concentration of adenosine in a patient's expired breath indicative of cardiovascular distress, the steps including:

containing a sample of expired breath from the patient;

shining a light through the sample of expired breath;

detecting and recording the light intensity before it has passed through the sample of expired breath;

detecting and recording the light intensity after it has passed through the sample of expired breath;

calculating the concentration of adenosine by utilizing the formula:

$$C = \frac{-\log_{10}(I_O/I_F)}{ab}$$

where C is the concentration of adenosine, $I_O$ is the light intensity before the light has passed through the sample of expired breath, $I_F$ is the light intensity after the light has passed through the sample of expired breath, a is the absorption constant, and b is the absorption path length.

* * * * *